US008637030B2

(12) United States Patent
Epshtein

(10) Patent No.: US 8,637,030 B2
(45) Date of Patent: Jan. 28, 2014

(54) COMBINATION PHARMACEUTICAL COMPOSITION AND METHODS OF TREATING FUNCTIONAL DISEASES OR CONDITIONS OF GASTROINTESTINAL TRACT

(75) Inventor: Oleg Iliich Epshtein, Moscow (RU)

(73) Assignee: Oleg I. Epshtein (RU)

( * ) Notice: Subject to any disclaimer, the term of this patent is extended or adjusted under 35 U.S.C. 154(b) by 43 days.

(21) Appl. No.: 13/135,888

(22) Filed: Jul. 15, 2011

(65) Prior Publication Data

US 2013/0004574 A1 Jan. 3, 2013

(30) Foreign Application Priority Data

Jul. 15, 2010 (RU) .................................. 2010129293
Jun. 20, 2011 (RU) .................................. 2011124809

(51) Int. Cl.
*A61K 39/395* (2006.01)
*C07K 16/18* (2006.01)
*C07K 16/22* (2006.01)
*C07K 16/24* (2006.01)
*C07K 16/26* (2006.01)

(52) U.S. Cl.
USPC ................ 424/145.1; 424/141.1; 424/158.1; 424/130.1; 530/387.1; 530/388.1; 530/388.23; 530/388.24

(58) Field of Classification Search
None
See application file for complete search history.

(56) References Cited

U.S. PATENT DOCUMENTS

| 4,311,897 | A | 1/1982 | Yerushalmy |
| 4,963,367 | A | 10/1990 | Ecanow |
| 4,987,127 | A | 1/1991 | Sirany |
| 5,629,286 | A | 5/1997 | Brewitt |
| 5,683,712 | A | 11/1997 | Cavazza |
| 5,698,195 | A | 12/1997 | Le et al. |
| 5,741,488 | A | 4/1998 | Feldman et al. |
| 5,846,514 | A | 12/1998 | Foster et al. |
| 5,879,677 | A | 3/1999 | Del Zoppo |
| 6,136,309 | A | 10/2000 | Novick et al. |
| 7,229,648 | B2 | 6/2007 | Dreyer |
| 7,572,441 | B2 | 8/2009 | Epshtein et al. |
| 7,582,294 | B2 | 9/2009 | Epshtein et al. |
| 2001/0006637 | A1 | 7/2001 | Akahoshi et al. |
| 2003/0099636 | A1 | 5/2003 | Epshtein et al. |
| 2007/0141058 | A1 | 6/2007 | Epshtein et al. |
| 2008/0025985 | A1 | 1/2008 | Epshtein et al. |

FOREIGN PATENT DOCUMENTS

| DE | 19746868 A1 | 4/1999 |
| EA | 008605 B1 | 6/2003 |
| EP | 0387095 A1 | 9/1990 |
| EP | 0652014 A1 | 5/1995 |
| EP | 0687466 A1 | 12/1995 |
| EP | 1466622 A1 | 10/2004 |
| RU | 2007989 C1 | 2/1994 |
| RU | 2033784 C1 | 4/1995 |
| RU | 2099052 C1 | 12/1997 |
| RU | 2104032 C1 | 2/1998 |
| RU | 2122858 C1 | 12/1998 |
| RU | 96118134 A | 12/1998 |
| RU | 2137483 C1 | 9/1999 |
| RU | 2177795 C1 | 1/2002 |
| RU | 2187334 C2 | 8/2002 |
| RU | 2192882 C1 | 11/2002 |
| RU | 2197266 C1 | 1/2003 |
| SU | 1730144 | 4/1992 |
| WO | 9412213 A1 | 6/1994 |
| WO | 9422846 | 10/1994 |
| WO | 95020978 A1 | 8/1995 |
| WO | 9728776 A1 | 8/1997 |
| WO | 9814161 A1 | 4/1998 |
| WO | 9814162 A1 | 4/1998 |
| WO | 9814166 A1 | 4/1998 |
| WO | 9833493 A1 | 8/1998 |
| WO | 9835680 A1 | 8/1998 |
| WO | 99/21582 A2 | 5/1999 |
| WO | 0105371 A1 | 1/2001 |
| WO | 03037372 A1 | 5/2003 |
| WO | 03055518 A1 | 7/2003 |
| WO | 03077946 A1 | 9/2003 |

OTHER PUBLICATIONS

Guggisberg Adrian G et al: "Replication study concerning the effects of homeopathic dilutions of histamine on human basophil degranulation in vitro.",Complementary Therapies in Medicine Jun. 2005 vol. 13, No. 2, Jun. 2005, pp. 91-100.

Shang A et al: "Are the clinical effects of homoeopathy placebo effects? Comparative study of placebo-controlled trials of homoeopathy and allopathy", The Lancet, Lancet Limited. London, GB, vol. 366, No. 9487, Aug. 27, 2005, pp. 726-732.

Jonas Wayne B et al: "A critical overview of homeopathy", Annals of Internal Medicine, New York, NY; US, US,vol. 138, No. 5, Mar. 4, 2003 pp. 393-399.

(Continued)

*Primary Examiner* — David Romeo
(74) *Attorney, Agent, or Firm* — Pergament Gilman & Cepeda LLP

(57) ABSTRACT

The present invention provides a combination pharmaceutical composition comprising a) an activated-potentiated form of an antibody to a S-100 protein, b) an activated-potentiated form of an antibody to histamine, and c) an activated-potentiated form of an antibody to TNF-alpha. Various embodiments and variants are provided. The present invention further provides a method of treating a disease or condition of functional etiology of the gastrointestinal tract, said method comprising administering to a patient in need thereof a combination pharmaceutical composition comprising a) an activated-potentiated form of an antibody to a histamine, b) an activated-potentiated form of an antibody to S-100 protein and c) an activated-potentiated form of an antibody to TNF-alpha. Various embodiments and variants are provided.

19 Claims, No Drawings

(56) References Cited

OTHER PUBLICATIONS

Vickers A J: "Clinical trials of homeopathy and placebo: Analysis of a scientific debate", Journal of Alternative and Complementary Medicine, Mary Ann Liebert, New York, NY, US, vol. 6, No. 1, Feb. 1, 2000, pp. 49-56.
International Search Report dated Feb. 14, 2012 for corresponding International Patent Application No. PCT/IB2011/002178.
Written Opinion of the International Searching Authority for corresponding International Patent Application No. PCT/IB2011/002178.
Notification of Transmittal of International Search Report and Written Opinion dated Feb. 24, 2012 for corresponding International Patent Application No. PCT/IB2011/002178.
Skurkovich, et al., "Randomized study of antibodies of IFN-g and TNF-a in secondary progressive multiple sclerosis", Multiple Sclerosis 2001, vol. 7, pp. 277-284.
Supplementary Partial European Search Report from corresponding European Application EP 02 75 9005 dated Feb. 2, 2006.
Luong B.T., et al., "Treatment Options for Rheumatoid Arthritis: Celecoxib, Leftunomide, Etanercept, and Infliximab", The Annals of Pharmacology, Jun. 2000, vol. 34, pp. 743-760.
Elliott, M.J., et al., "Randomised double-blind comparison of chimeric monoclonal antibody to tumor necrosis factor alpha (cA2) versus placebo in rheumatoid arthritis", Oct. 22, 1994, Lancet Little Brown and Co., Boston Massachusettes, US vol. 344, No. 8930, pp. 1105-1110.
Knight, D., et al., "Construction and Initial Characterization of a Mouse-Human Chimeric Anti-TNF Antibody" Molecular Immunology, 1993, vol. 30, No. 16, pp. 1443-1453.
Issekutz, A.C., et al., "The role of tumor necrosis factor-alpha and IL-1 in polymorphonuclear leucocyte and T lymphocyte recruitment to joint inflammation in adjuvant arthritis", Clinical and Experimental Immunology, 1994, vol. 97,pp. 26-32.
International Search Report from International Application No. PCT/RU02/00367, filed Aug. 2, 2002, mailed on Dec. 19, 2002.
Frimel, G., et al., "Immunological Methods," Medicine Publishing House, 1987, pp. 9-33.
Maini, R. N. et al., "Anti-Cytokine Therapy for Rheumatoid Arthritis, " Annu. Rev. Med., 2000; 51: 207-229.
Schwabe, W., "German Homeopathic Pharmacopoeia (Homoeopathisches Arzneibuch),"Stuttgart, Translation of the 5th Supplement (1991) to the 1978 edition.
Goldacre, B.,"Benefits and risks of homoeopathy", Lancet, Nov. 17, 2007 vol. 370, pp. 1672-1673.
Alexandrova, N. V. et al., "An Experience of Application of Potentiated Compounds for Jugulation of Alcohol Abstinent Syndrome and Opiate Abstinent Syndrome," Bulletin of Siberian Branch of RAMS, No. 1 (91), 1999.
Beregovoy, N. A. et al., "On Influence of Various Dilutions of Monoclonal Antibodies 5F5-B6 on the Formation of Long-Term Post-Tetanic Potentiation in Survived Hippocampal Slices", Bulletin of Siberian Branch of RAMS, No. 1 (91), 1999.
Davenas, E. et al., "Human basophil degranulation triggered by very dilute antiserum against IgE", Nature, vol. 333, Jun. 30, 1988 pp. 816-818.
Epshtein et al., "Effect of Potentiated Antibodies to Brain-Specific Protein S100 on the Integrative Activity of the Brain", May 1999, Bulletin of Experimental Biology and Medicine, vol. 5: pp. 493-495.
Grigoriev M. Yu. et al., "K probleme ispolzovaniya potentsirovannykh organnykh preparatov", Lechebno-profilakticheskaja Rabota Dlya Meditsinskikh Organizatsij V Ugolnoj Promyshlennosti, vyp. 8, 1989, izd. Tsniehi ugol (Moscow), pp. 163-165.
International Search Report from International Application No. PCT/RU01/00239, filed Jun. 19, 2001, mailed on Sep. 20, 2001.
International Search Report from International Application No. PCT/RU02/00365, filed Aug. 2, 2002, mailed on Dec. 5, 2002.
International Search Report from International Application No. PCT/RU04/000374, filed Sep. 27, 2004, mailed on Feb. 10, 2005.
International Search Report from International Application No. PCT/RU02/00368, filed Aug. 2, 2002, mailed on Dec. 5, 2002.
International Search Report from International Application No. PCT/RU02/00369, filed Aug. 2, 2002, mailed on Dec. 19, 2002.
International Search Report from International Application No. PCT/RU97/00026, filed Feb. 10, 1997, mailed on Apr. 8, 1997.
Ivaniushkin, A. Ja., "Gomeopatiya i sovremennaya meditsina", Vestnik Akademii Meditsinskikh Nauk SSSR, 4, 1988, izd. "Meditsina" (Moscow), pp. 76-82.
Janeway et al.: "Structure of the Antibody Molecule and Immunoglobulin Genes", Immunobiology, 1997, 3rd edition, Garland Publishing Inc. 3:1-3:11.
Jeger, J. Ed., "Clinical Immunology and Allergology" (Russian Translation), Meditsina, Moscow, 2000, pp. 358-359.
Kuznik, R.I. et al., "Cytomedines and their Role in Regulation of Physiological Functions", Institute of Bioregulation and Gerontology, Saint Petersburg, Russia, 1995, vol. 115, pp. 353-367.
Linde et al., "Are the clinical effects of homeopathy placebo effects? A meta-analysis of placebo-controlled trials", The Lancet, 1997, vol. 350: 834-43.
Nickeleit et al., "The classification and treatment of antibody mediated renal allograft injury. Where do we stand?", Kidney International, vol. 71, 2007, pp. 7-11.
Register of Pharmaceuticals of Russia, Encyclopedia of Pharmaceuticals (in Russian), Moscow, 2000, pp. 358-359.
Register of Pharmaceuticals of Russia, Encyclopedia of Pharmaceuticals (in Russian), Moscow, 2001, pp. 788-789.
Schwab, V., "Homeopathic Pharmaceutical Agents. A manual on description and preparation", Moscow, 1967, pp. 12-38.
Vyazov, O. L., Laboratory Methods of Studies in Non-Infection Immunology (in Russian) Moscow, Meditsina, 1968.
Stefani, D. V. et al., "Immunologiya i immunopatologiya detskogo vozrasta", Moscow, Meditsina, 1996, pp. 28, 29, 358-359.
Vasiliev, Yu, V. et al., "gomeopatiya: vozrozhdenie traditsionnioyy meditsinskoj shkoly", Vestnik Rossijkoj Adademii Nauk, 10, 1992, izd. "Nauka" (Moscow), pp. 145-148.

SEQUENCE LISTING

```
<160> NUMBER OF SEQ ID NOS: 16

<210> SEQ ID NO 1
<211> LENGTH: 233
```

```
<212> TYPE: PRT
<213> ORGANISM: Homo sapiens
<220> FEATURE:
<221> NAME/KEY: SOURCE
<222> LOCATION: 1..233
<223> OTHER INFORMATION: /mol_type="protein"
      /organism="Homo sapiens"

<400> SEQUENCE: 1

Met Ser Thr Glu Ser Met Ile Arg Asp Val Glu Leu Ala Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
                100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
            130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
            210                 215                 220

Gln Val Tyr Phe Gly Ile Ile Ala Leu
225                 230

<210> SEQ ID NO 2
<211> LENGTH: 5
<212> TYPE: PRT
<213> ORGANISM: Homo sapiens
<220> FEATURE:
<221> NAME/KEY: SOURCE
<222> LOCATION: 1..5
<223> OTHER INFORMATION: /mol_type="protein"
      /organism="Homo sapiens"

<400> SEQUENCE: 2

Pro Ser Asp Lys Pro
1               5

<210> SEQ ID NO 3
<211> LENGTH: 5
<212> TYPE: PRT
<213> ORGANISM: Homo sapiens
<220> FEATURE:
<221> NAME/KEY: SOURCE
<222> LOCATION: 1..5
<223> OTHER INFORMATION: /mol_type="protein"
```

/organism="Homo sapiens"

<400> SEQUENCE: 3

Val Ala Asn Pro Gln
1               5

<210> SEQ ID NO 4
<211> LENGTH: 135
<212> TYPE: PRT
<213> ORGANISM: Homo sapiens
<220> FEATURE:
<221> NAME/KEY: SOURCE
<222> LOCATION: 1..135
<223> OTHER INFORMATION: /mol_type="protein"
      /organism="Homo sapiens"

<400> SEQUENCE: 4

Arg Asp Leu Ser Leu Ile Ser Pro Leu Ala Gln Ala Val Arg Ser Ser
1               5                   10                  15

Ser Arg Thr Pro Ser Asp Lys Pro Val Ala His Val Val Ala Asn Pro
            20                  25                  30

Gln Ala Glu Gly Gln Leu Gln Trp Leu Asn Arg Arg Ala Asn Ala Leu
        35                  40                  45

Leu Ala Asn Gly Val Glu Leu Arg Asp Asn Gln Leu Val Val Pro Ser
    50                  55                  60

Glu Gly Leu Tyr Leu Ile Tyr Ser Gln Val Leu Phe Lys Gly Gln Gly
65                  70                  75                  80

Cys Pro Ser Thr His Val Leu Leu Thr His Thr Ile Ser Arg Ile Ala
                85                  90                  95

Val Ser Tyr Gln Thr Lys Val Asn Leu Leu Ser Ala Ile Lys Ser Pro
            100                 105                 110

Cys Gln Arg Glu Thr Pro Glu Gly Ala Glu Ala Lys Pro Trp Tyr Glu
        115                 120                 125

Pro Ile Tyr Leu Gly Gly Val
    130                 135

<210> SEQ ID NO 5
<211> LENGTH: 17
<212> TYPE: PRT
<213> ORGANISM: Homo sapiens
<220> FEATURE:
<221> NAME/KEY: SOURCE
<222> LOCATION: 1..17
<223> OTHER INFORMATION: /mol_type="protein"
      /organism="Homo sapiens"

<400> SEQUENCE: 5

Val Arg Ser Ser Ser Arg Thr Pro Ser Asp Lys Pro Val Ala His Val
1               5                   10                  15

Val

<210> SEQ ID NO 6
<211> LENGTH: 23
<212> TYPE: PRT
<213> ORGANISM: Homo sapiens
<220> FEATURE:
<221> NAME/KEY: SOURCE
<222> LOCATION: 1..23
<223> OTHER INFORMATION: /mol_type="protein"
      /organism="Homo sapiens"

<400> SEQUENCE: 6

Phe Leu Ser Leu Phe Ser Phe Leu Ile Val Ala Gly Ala Thr Thr Leu
1               5                   10                  15

```
Phe Cys Leu Leu His Phe Gly
            20
```

<210> SEQ ID NO 7
<211> LENGTH: 18
<212> TYPE: PRT
<213> ORGANISM: Homo sapiens
<220> FEATURE:
<221> NAME/KEY: SOURCE
<222> LOCATION: 1..18
<223> OTHER INFORMATION: /mol_type="protein"
      /organism="Homo sapiens"

<400> SEQUENCE: 7

```
Ile Gly Pro Gln Arg Glu Glu Phe Pro Arg Asp Leu Ser Leu Ile Ser
1               5                   10                  15

Pro Leu
```

<210> SEQ ID NO 8
<211> LENGTH: 38
<212> TYPE: PRT
<213> ORGANISM: Homo sapiens
<220> FEATURE:
<221> NAME/KEY: SOURCE
<222> LOCATION: 1..38
<223> OTHER INFORMATION: /mol_type="protein"
      /organism="Homo sapiens"

<400> SEQUENCE: 8

```
Gln Leu Val Val Pro Ser Glu Gly Leu Tyr Leu Ile Tyr Ser Gln Val
1               5                   10                  15

Leu Phe Lys Gly Gln Gly Cys Pro Ser Thr His Val Leu Leu Thr His
            20                  25                  30

Thr Ile Ser Arg Ile Ala
            35
```

<210> SEQ ID NO 9
<211> LENGTH: 15
<212> TYPE: PRT
<213> ORGANISM: Homo sapiens
<220> FEATURE:
<221> NAME/KEY: SOURCE
<222> LOCATION: 1..15
<223> OTHER INFORMATION: /mol_type="protein"
      /organism="Homo sapiens"

<400> SEQUENCE: 9

```
Pro Cys Gln Arg Glu Thr Pro Glu Gly Ala Glu Ala Lys Pro Trp
1               5                   10                  15
```

<210> SEQ ID NO 10
<211> LENGTH: 41
<212> TYPE: PRT
<213> ORGANISM: Homo sapiens
<220> FEATURE:
<221> NAME/KEY: SOURCE
<222> LOCATION: 1..41
<223> OTHER INFORMATION: /mol_type="protein"
      /organism="Homo sapiens"

<400> SEQUENCE: 10

```
Ser Met Ile Arg Asp Val Glu Leu Ala Glu Glu Ala Leu Pro Lys Lys
1               5                   10                  15

Thr Gly Gly Pro Gln Gly Ser Arg Arg Cys Leu Phe Leu Ser Leu Phe
            20                  25                  30

Ser Phe Leu Ile Val Ala Gly Ala Thr
```

```
                  35                  40
```

<210> SEQ ID NO 11
<211> LENGTH: 35
<212> TYPE: PRT
<213> ORGANISM: Homo sapiens
<220> FEATURE:
<221> NAME/KEY: SOURCE
<222> LOCATION: 1..35
<223> OTHER INFORMATION: /mol_type="protein"
      /organism="Homo sapiens"

<400> SEQUENCE: 11

```
Val Leu Leu Thr His Thr Ile Ser Arg Ile Ala Val Ser Tyr Gln Thr
1               5                   10                  15

Lys Val Asn Leu Leu Ser Ala Ile Lys Ser Pro Cys Gln Arg Glu Thr
            20                  25                  30

Pro Glu Gly
        35
```

<210> SEQ ID NO 12
<211> LENGTH: 157
<212> TYPE: PRT
<213> ORGANISM: Homo sapiens
<220> FEATURE:
<221> NAME/KEY: SOURCE
<222> LOCATION: 1..157
<223> OTHER INFORMATION: /mol_type="protein"
      /organism="Homo sapiens"

<400> SEQUENCE: 12

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

<210> SEQ ID NO 13
<211> LENGTH: 92
<212> TYPE: PRT
<213> ORGANISM: Bos taurus
<220> FEATURE:
<221> NAME/KEY: SOURCE
<222> LOCATION: 1..92
<223> OTHER INFORMATION: /mol_type="protein"
      /organism="Bos taurus"

<400> SEQUENCE: 13

```
Met Ser Glu Leu Glu Lys Ala Val Ala Leu Ile Asp Val Phe His
1               5                   10                  15

Gln Tyr Ser Gly Arg Glu Gly Asp Lys His Lys Leu Lys Lys Ser Glu
            20                  25                  30

Leu Lys Glu Leu Ile Asn Asn Glu Leu Ser His Phe Leu Glu Glu Ile
        35                  40                  45

Lys Glu Gln Glu Val Val Asp Lys Val Met Glu Thr Leu Asp Ser Asp
    50                  55                  60

Gly Asp Gly Glu Cys Asp Phe Gln Glu Phe Met Ala Phe Val Ala Met
65              70                  75                  80

Ile Thr Thr Ala Cys His Glu Phe Phe Glu His Glu
            85                  90
```

<210> SEQ ID NO 14
<211> LENGTH: 92
<212> TYPE: PRT
<213> ORGANISM: Homo sapiens
<220> FEATURE:
<221> NAME/KEY: SOURCE
<222> LOCATION: 1..92
<223> OTHER INFORMATION: /mol_type="protein"
      /organism="Homo sapiens"

<400> SEQUENCE: 14

```
Met Ser Glu Leu Glu Lys Ala Met Val Ala Leu Ile Asp Val Phe His
1               5                   10                  15

Gln Tyr Ser Gly Arg Glu Gly Asp Lys His Lys Leu Lys Lys Ser Glu
            20                  25                  30

Leu Lys Glu Leu Ile Asn Asn Glu Leu Ser His Phe Leu Glu Glu Ile
        35                  40                  45

Lys Glu Gln Glu Val Val Asp Lys Val Met Glu Thr Leu Asp Asn Asp
    50                  55                  60

Gly Asp Gly Glu Cys Asp Phe Gln Glu Phe Met Ala Phe Val Ala Met
65              70                  75                  80

Val Thr Thr Ala Cys His Glu Phe Phe Glu His Glu
            85                  90
```

<210> SEQ ID NO 15
<211> LENGTH: 94
<212> TYPE: PRT
<213> ORGANISM: Bos taurus
<220> FEATURE:
<221> NAME/KEY: SOURCE
<222> LOCATION: 1..94
<223> OTHER INFORMATION: /mol_type="protein"
      /organism="Bos taurus"

<400> SEQUENCE: 15

```
Met Gly Ser Glu Leu Glu Thr Ala Met Glu Thr Leu Ile Asn Val Phe
1               5                   10                  15

His Ala His Ser Gly Lys Glu Gly Asp Lys Tyr Lys Leu Ser Lys Lys
            20                  25                  30

Glu Leu Lys Glu Leu Leu Gln Thr Glu Leu Ser Gly Phe Leu Asp Ala
        35                  40                  45

Gln Lys Asp Val Asp Ala Val Asp Lys Val Met Lys Glu Leu Asp Glu
    50                  55                  60

Asn Gly Asp Gly Glu Val Asp Phe Gln Glu Tyr Val Val Leu Val Ala
65              70                  75                  80

Ala Leu Thr Val Ala Cys Asn Asn Phe Phe Trp Glu Asn Ser
            85                  90
```

```
<210> SEQ ID NO 16
<211> LENGTH: 94
<212> TYPE: PRT
<213> ORGANISM: Bos taurus
<220> FEATURE:
<221> NAME/KEY: SOURCE
<222> LOCATION: 1..94
<223> OTHER INFORMATION: /mol_type="protein"
      /organism="Bos taurus"

<400> SEQUENCE: 16

Met Gly Ser Glu Leu Glu Thr Ala Met Glu Thr Leu Ile Asn Val Phe
1               5                   10                  15

His Ala His Ser Gly Lys Glu Gly Asp Lys Tyr Lys Leu Ser Lys Lys
                20                  25                  30

Glu Leu Lys Glu Leu Leu Gln Thr Glu Leu Ser Gly Phe Leu Asp Ala
            35                  40                  45

Gln Lys Asp Ala Asp Ala Val Asp Lys Val Met Lys Glu Leu Asp Glu
        50                  55                  60

Asn Gly Asp Gly Glu Val Asp Phe Gln Glu Tyr Val Val Leu Val Ala
65                  70                  75                  80

Ala Leu Thr Val Ala Cys Asn Asn Phe Phe Trp Glu Asn Ser
                85                  90
```

COMBINATION PHARMACEUTICAL COMPOSITION AND METHODS OF TREATING FUNCTIONAL DISEASES OR CONDITIONS OF GASTROINTESTINAL TRACT

FIELD

The preset invention relates to a combination pharmaceutical compositions and method of treating functional diseases or conditions of gastrointestinal tract.

BACKGROUND

The invention relates to the area of medicine and may be used for the treatment of functional disorders or condition of gastrointestinal tract (GIT), including irritable bowel syndrome and disorders of the motor-evacuator function of the GIT, including the intestines.

Treatment of erosive and inflammatory diseases of the gastrointestinal tract based on ultra-low doses of histamine antibodies is known in the art (RU 2197266 C1). However, this pharmaceutical preparation cannot in all cases ensure sufficient therapeutic efficacy for treatment of functional bowel disorders.

The therapeutic effect of an extremely diluted form (or ultra-low form) of antibodies potentized by homeopathic technology (activated potentiated form) has been discovered by Dr. Oleg I. Epshtein. For example, U.S. Pat. No. 7,582,294 discloses a medicament for treating Benign Prostatic Hyperplasia or prostatitis by administration of a homeopathically activated form of antibodies to prostate specific antigen (PSA). Ultra-low doses of antibodies to gamma interferon have been shown to be useful in the treatment and prophylaxis of treating diseases of viral etiology. See U.S. Pat. No. 7,572,441, which is incorporated herein by reference in its entirety.

The S-100 protein is a cytoplasmic acidic calcium binding protein found predominantly in the gray matter of the brain, primarily in glia and Schwann cells. The protein exists in several homo- or heterodimeric isoforms consisting of two immunologically distinct subunits, alpha and beta. The S-100 protein has been suggested for use as an aid in the diagnosis and assessment of brain lesions and neurological damage due to brain injury, as in stroke. Yardan et al., Usefulness of S100B Protein in Neurological Disorders, J Pak Med Assoc Vol. 61, No. 3, March 2011, which is incorporated herein by reference.

Ultra-low doses of antibodies to S-100 protein have been shown to have anxiolytic, anti-asthenic, anti-aggressive, stress-protective, anti-hypoxic, anti-ischemic, neuroprotective and nootropic activity. See Castagne V. et al., *Antibodies to S100 proteins have anxiolytic-like activity at ultra-low doses in the adult rat*, J Pharm Pharmacol. 2008, 60(3):309-16; Epstein O. I., *Antibodies to calcium-binding S100B protein block the conditioning of long-term sensitization in the terrestrial snail*, Pharmacol Biochem Behav., 2009, 94(1):37-42; Voronina T. A. et al., Chapter 8. *Antibodies to S-100 protein in anxiety-depressive disorders in experimental and clinical conditions*. In "*Animal models in biological psychiatry*", Ed. Kalueff A. V. N-Y, "Nova Science Publishers, Inc.", 2006, pp. 137-152, all of which are incorporated herein by reference.

The present invention is directed to a combination pharmaceutical composition and methods of its use in treatment of functional disorders of gastrointestinal tract, including irritated bowel syndrome and disorders of the motor-evacuator function.

The solution to the existing problem is presented in form of a combination pharmaceutical composition for treatment and prophylaxis of diseases or conditions of functional etiology of the gastrointestinal tract which comprises activated-potentiated form of antibodies, to histamine activated-potentiated form of antibodies to tumor necrosis factor alpha (TNF-α) and activated-potentiated form of antibodies to brain-specific protein S-100.

SUMMARY

In one aspect, the invention provides a combination pharmaceutical composition comprising a) an activated-potentiated form of an antibody to S-100 protein, b) an activated-potentiated form of an antibody to histamine, and c) an activated-potentiated form of an antibody to TNF-alpha. In an embodiment, the combination pharmaceutical composition further comprises a solid carrier, wherein said activated-potentiated form an antibody to S-100 protein, said activated-potentiated form of an antibody to histamine, and said activated-potentiated form of an antibody to TNF-alpha are impregnated onto said solid carrier. In a variant, the combination pharmaceutical composition is in the form of a tablet.

Preferably, the combination pharmaceutical composition includes said activated-potentiated form of an antibody to S-100 protein is in the form of a mixture of C12, C30, and C200 homeopathic dilutions. It is specifically contemplated that said mixture of C12, C30, and C200 homeopathic dilutions is impregnated onto a solid carrier.

Preferably, the combination pharmaceutical composition includes said activated-potentiated form of an antibody to histamine is in the form of a mixture of C12, C30, and C200 homeopathic dilutions. It is specifically contemplated that said mixture of C12, C30, and C200 homeopathic dilutions is impregnated onto a solid carrier.

Preferably, the combination pharmaceutical composition includes said activated-potentiated form of an antibody to TNF-alpha is in the form of a mixture of C12, C30, and C200 homeopathic dilutions. It is specifically contemplated that said mixture of C12, C30, and C200 homeopathic dilutions is impregnated onto a solid carrier.

The activated-potentiated form of an antibody to histamine may be a monoclonal, polyclonal or natural antibody. It is specifically contemplated that the activated-potentiated form of an antibody to histamine is a polyclonal antibody. The activated-potentiated form of an antibody to S-100 protein may be a monoclonal, polyclonal or natural antibody. It is specifically contemplated that the activated-potentiated form of an antibody to S-100 protein is a polyclonal antibody. The activated-potentiated form of an antibody to TNF-alpha may be a monoclonal, polyclonal or natural antibody. It is specifically contemplated that the activated-potentiated form of an antibody to TNF-alpha is a polyclonal antibody. The invention provides activated-potentiated forms of antibodies to antigen(s) having sequences described in the specification and claimed in the appended claims.

In a variant, the combination pharmaceutical composition includes activated-potentiated form of an antibody to histamine prepared by successive centesimal dilutions coupled with shaking of every dilution. In a variant, the combination pharmaceutical composition includes activated-potentiated form of an antibody to S-100 protein prepared by successive centesimal dilutions coupled with shaking of every dilution. In a variant, the combination pharmaceutical composition includes activated-potentiated form of an antibody to TNF-alpha prepared by successive centesimal dilutions coupled with shaking of every dilution. Vertical shaking is specifically contemplated.

In another aspect, the invention provides a method of treating a disease or condition of functional etiology of the gastrointestinal tract, said method comprising administering to a patient in need thereof a) an activated-potentiated form of an antibody to histamine, b) an activated-potentiated form of an antibody to S-100 protein and c) an activated-potentiated form of an antibody to TNF-alpha. Preferably, the activated-potentiated form of an antibody to a histamine, the activated-potentiated form of an antibody to S-100 protein and the activated-potentiated form of an antibody to TNF-alpha are administered in the form of combined pharmaceutical composition.

It is contemplated that said disease or condition of functional etiology of the gastrointestinal tract is psychosomatic in nature. Preferably, said disease or condition of functional etiology of the gastrointestinal tract is irritable bowel syndrome. It is contemplated that said disease or condition of functional etiology of the gastrointestinal tract is abdominal pain. It is contemplated that said disease or condition of functional etiology of the gastrointestinal tract is diarrhea. It is contemplated that said disease or condition of functional etiology of the gastrointestinal tract is constipation. It is contemplated that said disease or condition of functional etiology of the gastrointestinal tract is a distortion in the motor-evacuatory function of the gastrointestinal tract.

In an embodiment, the combination pharmaceutical composition is administered in the form of a solid oral dosage form which comprises a pharmaceutically acceptable carrier and said activated-potentiated form of an antibody to histamine impregnated onto said carrier, said activated-potentiated form of an antibody to S-100 protein impregnated onto said carrier, and said activated-potentiated form of an antibody to TNF-alpha impregnated onto said carrier. In a variant, said solid oral dosage form is a tablet. Variants and embodiments are provided.

In accordance with the method aspect of the invention, the combination pharmaceutical composition may be administered in one to two unit dosage forms, each of the dosage form being administered from once daily to four times daily. In a variant, the combination pharmaceutical composition is administered twice daily, each administration consisting of two oral dosage form. In a variant, the combination pharmaceutical composition is administered in one to two unit dosage forms, each of the dosage forms being administered twice daily. All variants and embodiments described with respect to the composition aspect of the invention may be used with the method aspect of the invention. With respect to the method aspect of the invention, it is specifically contemplated that the administration of the combination of the invention may be accompanied by statistically significant reduction HADS score in the representative population of patients.

Co-administration of the combination pharmaceutical composition with an additional active ingredient is specifically contemplated. In a variant, the additional active ingredient is approved for treatment of irritable bowel syndrome. Variants and embodiments are contemplated.

DETAILED DESCRIPTION

The invention is defined with reference to the appended claims. With respect to the claims, the glossary that follows provides the relevant definitions.

The term "antibody" as used herein shall mean an immunoglobulin that specifically binds to, and is thereby defined as complementary with, a particular spatial and polar organization of another molecule. Antibodies as recited in the claims may include a complete immunoglobulin or fragment thereof, may be natural, polyclonal or monoclonal, and may include various classes and isotypes, such as IgA, IgD, IgE, IgG1, IgG2a, IgG2b and IgG3, IgM, etc. Fragments thereof may include Fab, Fv and F(ab')$_2$, Fab', and the like. The singular "antibody" includes plural "antibodies."

The term "activated-potentiated form" or "potentiated form" respectively, with respect to antibodies recited herein is used to denote a product of homeopathic potentization of any initial solution of antibodies. "Homeopathic potentization" denotes the use of methods of homeopathy to impart homeopathic potency to an initial solution of relevant substance. Although not so limited, 'homeopathic potentization" may involve, for example, repeated consecutive dilutions combined with external treatment, particularly vertical (mechanical) shaking. In other words, an initial solution of antibody is subjected to consecutive repeated dilution and multiple vertical shaking of each obtained solution in accordance with homeopathic technology. The preferred concentration of the initial solution of antibody in the solvent, preferably water or a water-ethyl alcohol mixture, ranges from about 0.5 to about 5.0 mg/ml. The preferred procedure for preparing each component, i.e. antibody solution, is the use of the mixture of three aqueous or aqueous-alcohol dilutions of the primary matrix solution (mother tincture) of antibodies diluted $100^{12}$, $100^{30}$ and $100^{200}$ times, respectively, which is equivalent to centesimal homeopathic dilutions (C12, C30, and C200) or the use of the mixture of three aqueous or aqueous-alcohol dilutions of the primary matrix solution of antibodies diluted $100^{12}$, $100^{30}$ and $100^{50}$ times, respectively, which is equivalent to centesimal homeopathic dilutions (C12, C30 and C50). Examples of homeopathic potentization are described in U.S. Pat. Nos. 7,572,441 and 7,582,294, which are incorporated herein by reference in their entirety and for the purpose stated. While the term "activated-potentiated form" is used in the claims, the term "ultra-low doses" is used in the examples. The term "ultra-low doses" became a term of art in the field of art created by study and use of homeopathically diluted and potentized form of substance. The term "ultra-low dose" or "ultra-low doses" is meant as fully supportive and primarily synonymous with the term 'activated-potentiated" form used in the claims.

In other words, an antibody is in the "activated-potentiated" or "potentiated" form when three factors are present. First, the "activated-potentiated" form of the antibody is a product of a preparation process well accepted in the homeopathic art. Second, the "activated-potentiated" form of antibody must have biological activity determined by methods well accepted in modern pharmacology. And third, the biological activity exhibited by the "activated potentiated" form of the antibody cannot be explained by the presence of the molecular form of the antibody in the final product of the homeopathic process.

For example, the activated potentiated form of antibodies may be prepared by subjecting an initial, isolated antibody in a molecular form to consecutive multiple dilutions coupled with an external impact, such as mechanical shaking. The external treatment in the course of concentration reduction may also be accomplished, for example, by exposure to ultrasonic, electromagnetic, or other physical factors. V. Schwabe "Homeopathic medicines", M., 1967, U.S. Pat. Nos. 7,229,648 and 4,311,897, which are incorporated by reference in their entirety and for the purpose stated, describe such processes that are well-accepted methods of homeopathic potentiation in the homeopathic art. This procedure gives rise to a uniform decrease in molecular concentration of the initial molecular form of the antibody. This procedure is repeated until the desired homeopathic potency is obtained. For the individual antibody, the required homeopathic potency can be determined by subjecting the intermediate dilutions to biological testing in the desired pharmacological model. Although not so limited, 'homeopathic potentization" may involve, for example, repeated consecutive dilutions combined with external treatment, particularly vertical (mechanical) shaking. In other words, an initial solution of antibody is subjected to consecutive repeated dilution and multiple vertical shaking of each obtained solution in accordance with homeopathic technology. The preferred concentration of the initial solution of antibody in the solvent, preferably, water or a water-ethyl alcohol mixture, ranges from about 0.5 to about 5.0 mg/ml. The preferred procedure for preparing each component, i.e. antibody solution, is the use of the mixture of three aqueous or aqueous-alcohol dilutions of the primary matrix solution (mother tincture) of antibodies diluted $100^{12}$, $100^{30}$ and $100^{200}$ times, respectively, which is equivalent to centesimal homeopathic dilutions C12, C30 and C200 or the mixture of three aqueous or aqueous-alcohol dilutions of the primary matrix solution (mother tincture) of antibodies diluted $100^{12}$, $100^{30}$ and $100^{50}$ times, respectively, which is equivalent to centesimal homeopathic dilutions C12, C30 and C50. Examples of how to obtain the desired potency are also provided, for example, in U.S. Pat. Nos. 7,229,648 and 4,311,897, which are incorporated by reference for the purpose stated. The procedure applicable to the "activated-potentiated" form of the antibodies described herein is described in more detail below.

There has been a considerable amount of controversy regarding homeopathic treatment of human subjects. While the present invention relies on accepted homeopathic processes to obtain the "activated-potentiated" form of antibodies, it does not rely solely on homeopathy in human subjects for evidence of activity. It has been surprisingly discovered by the inventor of the present application and amply demonstrated in the accepted pharmacological models that the solvent ultimately obtained from consecutive multiple dilution of a starting molecular form of an antibody has definitive activity unrelated to the presence of the traces of the molecular form of the antibody in the target dilution. The "activated-potentiated" form of the antibody provided herein is tested for biological activity in well accepted pharmacological models of activity, either in appropriate in vitro experiments, or in vivo in suitable animal models. The experiments provided further below provide evidence of biological activity in such models. Human clinical studies also provide evidence that the activity observed in the animal model is well translated to human therapy. Human studies have also provided evidence of availability of the "activated potentiated" forms described herein to treat specified human diseases or disorders well accepted as pathological conditions in the medical science.

Also, the claimed "activated-potentiated" form of antibody encompasses only solutions or solid preparations the biological activity of which cannot be explained by the presence of the molecular form of the antibody remaining from the initial, starting solution. In other words, while it is contemplated that the "activated-potentiated" form of the antibody may contain traces of the initial molecular form of the antibody, one skilled in the art could not attribute the observed biological activity in the accepted pharmacological models to the remaining molecular form of the antibody with any degree of plausibility due to the extremely low concentrations of the molecular form of the antibody remaining after the consecutive dilutions. While the invention is not limited by any specific theory, the biological activity of the "activated-potentiated' form of the antibodies of the present invention is not attributable to the initial molecular form of the antibody. Preferred is the "activated-potentiated" form of antibody in liquid or solid form in which the concentration of the molecular form of the antibody is below the limit of detection of the accepted analytical techniques, such as capillary electrophoresis and High Performance Liquid Chromatography. Particularly preferred is the "activated-potentiated" form of antibody in liquid or solid form in which the concentration of the molecular form of the antibody is below the Avogadro number. In the pharmacology of molecular forms of therapeutic substances, it is common practice to create a dose-response curve in which the level of pharmacological response is plotted against the concentration of the active drug administered to the subject or tested in vitro. The minimal level of the drug which produces any detectable response is known as a threshold dose. It is specifically contemplated and preferred that the "activated-potentiated" form of the antibodies contains molecular antibody, if any, at a concentration below the threshold dose for the molecular form of the antibody in the given biological model.

The term "disease or condition of functional etiology of the gastrointestinal tract" or "functional bowel disorder" should be understood to encompass such diseases or conditions of the GIT, including the intestine, when there exists a disorder in the function of the GIT which interferes with the functioning of the patient to any noticeable degree. But in particular, this term is meant to define disorders or condition which are observed and experienced not as a result of organic injury, but in terms of nervous, psychosomatic, and/or humoral disturbance in the regulation of the activity of the digestive tract (e.g., when organic intestinal injury is either completely absent or plays a secondary role in decease etiology and/or patient experience). Functional bowel disorders are characterized by the absence of morphological changes (by means of which it would have been possible to explain the clinical symptoms) and by their connection, first, with increased excitability, secondly, with sensory hypersensitivity and, thirdly, with inadequate reaction of internal organs to signals of the central nervous system under the influence of psychosocial factors.

Functional bowel disorders are the most frequent form of functional pathology of the gastrointestinal tract and are noted in 40-70% of patients of the gastroenterological profile. Development of functional bowel disorders is believed to be affected by genetic factors, environmental factors, psychosocial factors, visceral hypersensitivity and infections. Functional bowel disorders are part of the large group of gastrointestinal tract diseases that relate to functional pathology and, according to the classification of functional bowel disorders (Roman Consensus, 1999), they include such clinical conditions as irritable bowel syndrome (IBS), functional flatulence, functional constipation, functional diarrhea and nonspecific functional bowel disorders.

In the pathogenesis of these diseases, motor function disturbances of the stomach and intestine are believed to play an essential role. A particular feature of patients with functional bowel disorders is an increase in motor and sensory reaction(s), and the appearance of abdominal pain in response to stresses. The symptoms of functional bowel disorders includes complaints of abdominal pain (usually decreasing after defecation), flatulence, grumbling, feeling of incomplete emptying of the intestine, imperative urges to defecate, constipation, diarrheas or their alternation and/or combination. The clinical features characteristic of all functional disorders of the gastrointestinal tract include the prolonged (usually many years) course of the disease without noticeable progression; the breadth and variety in the presentation of the clinical picture (combination of stomach pains, dyspeptic disorders and disturbances of intestinal functions with migraine-type headaches, sleep disorders, sensation of coma with ingestion, dissatisfaction of inhalation, impossibility of sleeping on the left side, more frequent urination, various spasmic colon reactions and other vegetative disorders); the variable nature of complaints; the connection of worsening health with psycho-emotional factors.

Irritated bowel syndrome (IBS) is one of the most frequently encountered functional bowel disorders, found, as observations of the latest years show, both in Third World countries and in developed countries. The prevalence of IBS in the majority of countries in the world is, on average, 20%, varying, according to the data of different studies, from 9 to 48%. Morbidity peaks during young working age, 30-40 years. The ratio of women to men varies from 1:1 to 2:1. Among men after 50 years of age, IBS is as widespread as among women. The average age of patients is 24-41 years. The irritated bowel syndrome (IBS) is one of the most frequently encountered diseases of modern man.

The etiology and pathogenesis of IBS are complex and not fully understood. Most researchers agree that psychoemotional stress plays about an important role in the development of IBS. Depending on the predominant symptom(s), three possible courses of IBS may be distinguished: with predominant abdominal pains and flatulence, with predominant diarrhea, and with predominant constipation.

Until 1988, IBS was described by different names, such as spastic colitis, mucous colic, nervous diarrhea, irritated large intestine, functional intestinal distress syndrome and others. These names reflected different symptoms of the disease and did not reflect uniform understanding of the problem. In 1988 in Rome, the International Study Group for Functional Disorders of the Gastrointestinal Tract (GIT) for the first time officially confirmed the expression "irritated bowel syndrome," gave its definition and developed criteria for formulating the diagnosis, which was called subsequently called "Roman criteria for IBS." In 1999, the criteria were supplemented and called "Roman II criteria for IBS". In accordance with "Roman II criteria," IBS is a firm set of functional disorders lasting not less than 12 weeks in the course of the last 12 months that manifest stomach pain and/or discomfort, which pass after defecation, are accompanied by changes in the frequency and consistency of stools and combine during 25% of the time of the disease with no less than two stable symptoms of disturbance of intestinal function—by changes in the frequency of stools, the consistency of feces, the very act of defecation (imperative urges, tenesmus, a feeling of incomplete bowel evacuation, extra effort on defecation), by secretion of mucus with feces and flatulence.

In treating this syndrome, among the other preparations actively used are regulators of the intestine motor activity and spasmolytic agents.

The present invention provides a combination pharmaceutical composition that includes activated-potentiated forms of antibodies to histamine, TNF-α and brain-specific protein S-100, each may be prepared according to the homeopathic technology of potentiation by repeated, consistent dilution and intermediate external action of shaking as described in more detail herein below. The combination pharmaceutical composition of the invention is particularly useful in the treatment of functional bowel disorders. As shown in the Examples, the combination pharmaceutical composition of the invention possesses unexpected synergetic therapeutic effect, which manifest itself in particular therapeutic effectiveness in treatment of functional bowel disorders, in particular, irritated bowel syndrome, disorders of the motor-evacuator function of GIT, including the intestine, constipation, diarrhea, and other disorder of similar etiology. The effect of the combination pharmaceutical composition, as shown in well-accepted and adequate experimental models, manifests itself, e.g., in normalization of nervous, psychosomatic, and humoral regulation of intestinal function, reduction of visceral hypersensitivity to distension of large intestine receptors, which leads to restoration of intestinal locomotor system disturbance, curtailment of the sensation of abdominal bulging and overfilling of stomach, decreased manifestations of abdominal pain syndrome. Alongside, there occurs weakening of smooth musculature, decrease of tone of gastrointestinal tract (GIT) wall, drop in intra-aperture pressure, normalization of stool consistency, its frequency and the associated symptoms (curtailment of imperative urges, false urge to defecate, feeling of incomplete emptying of intestine, extra efforts upon defecation and others).

It is specifically contemplated that the combination pharmaceutical composition of the invention may be used in combination with other active ingredients, particularly those used for treatment of diseases or conditions of the GIT. Non-limiting examples of suitable additional active ingredients include 5-HT3 antagonists, such as Alosetron, Cilansetron, Ramosetron, 5-HT4 antagonists, such as Tegaserod, mixed 5-HT4 agonist/5-HT3 antagonists, such as Renzapride and Mosapride, Opioid agents, such as alvimopan and asimadoline, CRH (Corticotropin-releasing hormone) receptor antagonists, chloride channel activators, such as Lubiprostone, CCK (Cholecystokinin) antagonists, such as Dexloxiglumide, neurokinin antagonists, antidepressants, including tricyclic antidepressants, such as Amitriptyline, Clomipramine, Demexiptiline, Imipramine, Lofepramine, Metapramine, Nitroxazepine, Nortriptyline, Pipofezine, Propizepine, Protriptyline, and Quinupramine, SSRIs, such as citalopram, dapoxetine, escitalopram, fluoxetine, fluvoxamine, paroxetine, sertraline, vilazodone, antispasmodics, anticholinergics/antimuscarinic agents (e.g. hyoscyamine, dicyclomine, cimetropium), direct smooth muscle relaxing agents (e.g. mebeverine, pinaverine, octylonium bromide), antidiarrheals, for example, loperamide, benzodiazepines, for example, bextofisopam, and antibiotics, such as lincosamides, cephalosporins, ansamycins, aminoglycosides, penicillins, quinolones, sulfonamides, tetracyclines, macrolides, lincosamides, monobactams, and nitrofurans.

The pharmaceutical composition of the invention expands the arsenal of preparations available for the treatment and prophylaxis of functional bowel disorders.

Polyclonal antibodies to histamine, which is a biogenic amine (4(2-aminoethyl)-imidazole or beta-imidazolylethylamine with the chemical formula $C_5H_9N_3$), may be obtained by using adjuvant and industrially produced histamine dihydrochloride as immunogen (antigen) for immunization of rabbits.

Before taking blood, 1-3 intravenous injections are done over 7-9 days to increase the level of antibodies. In the immunization process in rabbits, small blood samples are taken for evaluating the quantity of antibodies. The maximum level of immune response to the introduction of the majority of soluble antigens is reached 40-60 days after the first injection. After the end of the first cycle of rabbit immunization, in the course of 30 days, health is allowed to be restored and reimmunization is carried out, which includes 1-3 intravenous injections. To obtain antiserum from immunized rabbits, blood is collected in a centrifugal test tube in the volume of 50 ml. With the help of a wooden spatula, formed clots are removed from the test tube walls and a stick is placed in the clot formed in the center of test tube. The blood is placed in a cooler (temperature 40° C.) for the night. On the next day, the clot that fastened to the spatula is removed, and the remained fluid is centrifuged at 13000 g for 10 min. The supernatant (supernatant fluid) is antiserum. The antiserum obtained should be of yellow color. To the antiserum is added 20% (weight concentration) $NaN_3$ to the final concentration of 0.02%, and it is stored until use in frozen condition at a temperature of −20° C., or without $NaN_3$ at a temperature of −70° C. For separating the antiserum of histamine antibodies, solid phase absorption is carried out in the following sequence:
1. 10 ml of rabbit antiserum is diluted 2 times with 0.15 M NaCl, 6.26 g of $Na_2SO_4$ is added, it is mixed and incubated 12-16 hr at 4° C.;
2. the fallen precipitation is removed by centrifuging, dissolves in 10 ml of phosphate buffer and then dialyzed against the same buffer overnight at room temperature;
3. after removal of precipitation by centrifuging, the solution is applied to the column with DEAE-cellulose, balanced by phosphate buffer;
4. the fraction of antibodies is determined, measuring the optical density of the eluate at 280 nm.

Then the antibodies are purified by the affine chromatography method via fastening of obtained antibodies to histamine, which is found in the un-dissolved matrix with subsequent elution by the concentrated salt solutions.

The buffer solution of polyclonal rabbit antibody to histamine so obtained, purified on antigen, with concentration of 0.5-5.0 mg/ml, preferably 2.0-3.0 mg/ml, is used as the matrix (primary) solution for subsequent preparation of the activated-potentiated form.

Polyclonal antibodies to tumor necrosis factor alpha (TNF-α) may be obtained by the above-mentioned method of obtaining polyclonal histamine antibodies using a whole molecule of tumor necrosis factor alpha of the following sequence:

```
                                          SEQ. ID. NO. 1
        Met Ser Thr Glu Ser Met Ile Arg Asp Val Glu Leu Ala Glu Glu
        1               5                   10                  15

Ala Leu Pro Lys Lys Thr Gly Gly Pro Gln Gly Ser Arg Arg Cys
        16              20                  25                  30

Leu Phe Leu Ser Leu Phe Ser Phe Leu Ile Val Ala Gly Ala Thr
        31              35                  40                  45

Thr Leu Phe Cys Leu Leu His Phe Gly Val Ile Gly Pro Gln Arg
        46              50                  55                  60

Glu Glu Phe Pro Arg Asp Leu Ser Leu Ile Ser Pro Leu Ala Gln
        61              65                  70                  75

Ala Val Arg Ser Ser Ser Arg Thr Pro Ser Asp Lys Pro Val Ala
        76              80                  85                  90

His Val Val Ala Asn Pro Gln Ala Glu Gly Gln Leu Gln Trp Leu
        91              95                  100                 105

Asn Arg Arg Ala Asn Ala Leu Leu Ala Asn Gly Val Glu Leu Arg
        106             110                 115                 120

Asp Asn Gln Leu Val Val Pro Ser Glu Gly Leu Tyr Leu Ile Tyr
        121             125                 130                 135

Ser Gln Val Leu Phe Lys Gly Gln Gly Cys Pro Ser Thr His Val
        136             140                 145                 150

Leu Leu Thr His Thr Ile Ser Arg Ile Ala Val Ser Tyr Gln Thr
        151             155                 160                 165

Lys Val Asn Leu Leu Ser Ala Ile Lys Ser Pro Cys Gln Arg Glu
        166             170                 175                 180

Thr Pro Glu Gly Ala Glu Ala Lys Pro Trp Tyr Glu Pro Ile Tyr
        181             185                 190                 195

Leu Gly Gly Val Phe Gln Leu Glu Lys Gly Asp Arg Leu Ser Ala
        196             200                 205                 210

Glu Ile Asn Arg Pro Asp Tyr Leu Asp Phe Ala Glu Ser Gly Gln
        211             215                 220                 225

Val Tyr Phe Gly Ile Ile Ala Leu
        226             230         233
```

To obtain polyclonal antibodies to tumor necrosis factor alpha (TNF-α), it is also possible to use a polypeptide fragment of the tumor necrosis factor, selected, for example, from the following sequences:

```
                                                    SEQ. ID. NO. 2
Pro Ser Asp Lys Pro
84              88

SEQ. ID. NO. 3
Val Ala Asn Pro Gln
93              97

SEQ. ID. NO. 4
                Arg Asp Leu Ser Leu Ile Ser Pro Leu Ala Gln
                65              70                      75

Ala Val Arg Ser Ser Ser Arg Thr Pro Ser Asp Lys Pro Val Ala
76              80              85                      90

His Val Val Ala Asn Pro Gln Ala Glu Gly Gln Leu Gln Trp Leu
91              95              100                     105

Asn Arg Arg Ala Asn Ala Leu Leu Ala Asn Gly Val Glu Leu Arg
106             110             115                     120

Asp Asn Gln Leu Val Val Pro Ser Glu Gly Leu Tyr Leu Ile Tyr
121             125             130                     135

Ser Gln Val Leu Phe Lys Gly Gln Gly Cys Pro Ser Thr His Val
136             140             145                     150

Leu Leu Thr His Thr Ile Ser Arg Ile Ala Val Ser Tyr Gln Thr
151             155             160                     165

Lys Val Asn Leu Leu Ser Ala Ile Lys Ser Pro Cys Gln Arg Glu
166             170             175                     180

Thr Pro Glu Gly Ala Glu Ala Lys Pro Trp Tyr Glu Pro Ile Tyr
181             185             190                     195

Leu Gly Gly Val
196         199

SEQ. ID. NO. 5
    Val Arg Ser Ser Ser Arg Thr Pro Ser Asp Lys Pro Val Ala
        77              80              85                  90

His Val Val
91      93

SEQ. ID. NO. 6
    Phe Leu Ser Leu Phe Ser Phe Leu Ile Val Ala Gly Ala Thr
        32              35              40                  45

Thr Leu Phe Cys Leu Leu His Phe Gly
46              50              54

SEQ. ID. NO 7
56-73
                                Ile Gly Pro Gln Arg
                                56                60

Glu Glu Phe Pro Arg Asp Leu Ser Leu Ile Ser Pro Leu.
61              65              70          73

SEQ. ID. NO 8
123-160
            Gln Leu Val Val Pro Ser Glu Gly Leu Tyr Leu Ile Tyr
                123     125             130                 135

Ser Gln Val Leu Phe Lys Gly Gln Gly Cys Pro Ser Thr His Val
136             140             145                     150

Leu Leu Thr His Thr Ile Ser Arg Ile Ala.
151             155             160
```

-continued

```
                                                    SEQ. ID. NO 9
176-190
                                        Pro Cys Gln Arg Glu
                                        176             180

Thr Pro Glu Gly Ala Glu Ala Lys Pro Trp.
181             185             190

SEQ. ID. NO 10
5-45
                Ser Met Ile Arg Asp Val Glu Leu Ala Glu
                 5                  10              15

Ala Leu Pro Lys Lys Thr Gly Gly Pro Gln Gly Ser Arg Arg Cys
 16              20              25              30

Leu Phe Leu Ser Leu Phe Ser Phe Leu Ile Val Ala Gly Ala Thr.
 31              35              40              45

SEQ. ID. NO 11
150-184
                                                        Val
                                                        150

Leu Leu Thr His Thr Ile Ser Arg Ile Ala Val Ser Tyr Gln Thr
151              155             160             165

Lys Val Asn Leu Leu Ser Ala Ile Lys Ser Pro Cys Gln Arg Glu
166              170             175             180

Thr Pro Glu Gly.
181         184

SEQ. ID. NO 12
77-233
    Val Arg Ser Ser Ser Arg Thr Pro Ser Asp Lys Pro Val Ala
     77          80              85              90

His Val Val Ala Asn Pro Gln Ala Glu Gly Gln Leu Gln Trp Leu
 91              95              100             105

Asn Arg Arg Ala Asn Ala Leu Leu Ala Asn Gly Val Glu Leu Arg
106              110             115             120

Asp Asn Gln Leu Val Val Pro Ser Glu Gly Leu Tyr Leu Ile Tyr
121              125             130             135

Ser Gln Val Leu Phe Lys Gly Gln Gly Cys Pro Ser Thr His Val
136              140             145             150

Leu Leu Thr His Thr Ile Ser Arg Ile Ala Val Ser Tyr Gln Thr
151              155             160             165

Lys Val Asn Leu Leu Ser Ala Ile Lys Ser Pro Cys Gln Arg Glu
166              170             175             180

Thr Pro Glu Gly Ala Glu Ala Lys Pro Trp Tyr Glu Pro Ile Tyr
181              185             190             195

Leu Gly Gly Val Phe Gln Leu Glu Lys Gly Asp Arg Leu Ser Ala
196              200             205             210

Glu Ile Asn Arg Pro Asp Tyr Leu Asp Phe Ala Glu Ser Gly Gln
211              215             220             225

Val Tyr Phe Gly Ile Ile Ala Leu.
226              230         233
```

The brain-specific S100 protein, expressed by neurons and glial cells (astrocytes and oligodendrocytes), directly or through interactions with other proteins executes in the CNS a number of functions directed at maintaining normal brain functioning, including affecting learning and memory processes, growth and viability of neurons, regulation of metabolic processes in neuronal tissues and others. To prepare the activated-potentiated form of antibodies, an antiserum to the brain-specific protein S-100 may be removed from the brain tissue of a bull and processed as follows:

the bull brain tissue frozen in liquid nitrogen is converted into powder using a specialized mill;

proteins are extracted in the ratio of 1:3 (weight/volume) using an extracting buffer with homogenization;

the homogenate is heated for 10 min at 60° C. and then cooled to 4° C. in an ice bath;

thermolabile proteins are removed by centrifugation;

ammonium sulfate fractionation is carried out in stages, with subsequent removal of precipitated proteins;

the fraction containing S-100 protein is precipitated using 100% saturated ammonium sulfate accomplished by pH drop to 4.0; the desired fraction is collected by centrifugation;

the precipitate is dissolved in a minimum buffer volume containing EDTA and mercaptoethanol, the precipitate is dialyzed with deionized water and lyophilized;

fractionation of acidic proteins is followed by chromatography in ion-exchanging media, DEAE-cellulose DE-52 and then DEAE-sephadex A-50;

the collected and dialyzed fractions, which contain S-100 protein, are divided according to molecular weight by gel filtration on sephadex G-100;

purified S-100 protein is dialyzed and lyophilized.

The molecular weight of the purified brain-specific protein S-100 is 21000 D.

The polyclonal antibodies to S-100 protein may also be obtained by a similar methodology to the methodology described for histamine antibodies using an adjuvant. The entire molecule of S-100 protein may be used as immunogen (antigen) for rabbits' immunization.

```
Bovine S100B
                                                            (SEQ. ID. NO. 13)
Met Ser Glu Leu Glu Lys Ala Val Val Ala Leu Ile Asp Val Phe
 1           5                   10                      15

His Gln Tyr Ser Gly Arg Glu Gly Asp Lys His Lys Leu Lys Lys
16              20                  25                  30

Ser Glu Leu Lys Glu Leu Ile Asn Asn Glu Leu Ser His Phe Leu
31              35                  40                  45

Glu Glu Ile Lys Glu Gln Glu Val Val Asp Lys Val Met Glu Thr
46              50                  55                  60

Leu Asp Ser Asp Gly Asp Gly Glu Cys Asp Phe Gln Glu Phe Met
61              65                  70                  75

Ala Phe Val Ala Met Ile Thr Thr Ala Cys His Glu Phe Phe Glu
76              80                  85                  90

His Glu
91  92

Human S100B
                                                            (SEQ. ID. 14)
Met Ser Glu Leu Glu Lys Ala Met Val Ala Leu Ile Asp Val Phe
 1           5                   10                      15

His Gln Tyr Ser Gly Arg Glu Gly Asp Lys His Lys Leu Lys Lys
16              20                  25                  30

Ser Glu Leu Lys Glu Leu Ile Asn Asn Glu Leu Ser His Phe Leu
31              35                  40                  45

Glu Glu Ile Lys Glu Gln Glu Val Val Asp Lys Val Net Glu Thr
46              50                  55                  60

Leu Asp Asn Asp Gly Asp Gly Glu Cys Asp Phe Gln Glu Phe Met
61              65                  70                  75

Ala Phe Val Ala Met Val Thr Thr Ala Cys His Glu Phe Phe Glu
76              80                  85                  90

His Glu
91  92

Human S100A1
                                                            (SEQ. ID. No. 15)
Met Gly Ser Glu Leu Glu Thr Ala Met Glu Thr Leu Ile Asn Val
 1           5                   10                      15

Phe His Ala His Ser Gly Lys Glu Gly Asp Lys Tyr Lys Leu Ser
16              20                  25                  30

Lys Lys Glu Leu Lys Glu Leu Leu Gln Thr Glu Leu Ser Gly Phe
31              35                  40                  45

Leu Asp Ala Gln Lys Asp Val Asp Ala Val Asp Lys Val Met Lys
46              50                  55                  60

Glu Leu Asp Glu Asn Gly Asp Gly Glu Val Asp Phe Gln Glu Tyr
61              65                  70                  75

Val Val Leu Val Ala Ala Leu Thr Val Ala Cys Asn Asn Phe Phe
76              80                  85                  90

Trp Glu Asn Ser
```

-continued

Bovine S100A1 (SEQ. ID. NO. 16)

```
Met Gly Ser Glu Leu Glu Thr Ala Met Glu Thr Leu Ile Asn Val
 1               5                  10                  15

Phe His Ala His Ser Gly Lys Glu Gly Asp Lys Tyr Lys Leu Ser
16              20                  25                  30

Lys Lys Glu Leu Lys Glu Leu Leu Gln Thr Glu Leu Ser Gly Phe
31              35                  40                  45

Leu Asp Ala Gln Lys Asp Ala Asp Ala Val Asp Lys Val Met Lys
46              50                  55                  60

Glu Leu Asp Glu Asn Gly Asp Gly Glu Val Asp Phe Gln Glu Tyr
61              65                  70                  75

Val Val Leu Val Ala Ala Leu Thr Val Ala Cys Asn Asn Phe Phe
76              80                  85                  90

Trp Glu Asn Ser
91              94
```

To obtain brain-specific antiserum to separated brain-specific protein S-100, a mixture of purified S-100 protein (antigen) may be prepared in complex by methylated bull serum albumin as the medium with complete Freund's adjuvant, which is subcutaneously injected in the laboratory animal, rabbit, in the area of the spine in the quantity of 1-2 ml. The antiserum may have a titer of 1:500-1:1000.

For preparing the components of the combination pharmaceutical composition, it is preferable to use polyclonal antibodies to histamine, TNF-α and brain-specific protein S-100 using the initial, matrix (primary) solution with concentration of 0.5÷5.0 mg/ml (preferably, 2.0÷3.0 mg/ml). Subsequently, the matrix solution is diluted as described in more details below to prepare the activated-potentiated form of the component.

The combination pharmaceutical composition may be in the liquid form or in solid form. Each of the activated-potentiated forms of the antibodies included in the pharmaceutical composition is prepared from an initial molecular form of the antibody via a process accepted in homeopathic art. The starting antibodies may be monoclonal, or polyclonal antibodies prepared in accordance with known processes, for example, as described in Immunotechniques, G. Frimel, M., "Meditsyna", 1987, p. 9-33; "Hum. Antibodies. Monoclonal and recombinant antibodies, 30 years after" by Laffly E., Sodoyer R.—2005—Vol. 14.—N 1-2. P. 33-55, both incorporated herein by reference.

Monoclonal antibodies may be obtained, e.g., by means of hybridoma technology. The initial stage of the process includes immunization based on the principles already developed in the course of polyclonal antisera preparation. Further stages of work involve the production of hybrid cells generating clones of antibodies with identical specificity. Their separate isolation is performed using the same methods as in the case of polyclonal antisera preparation.

Polyclonal antibodies may be obtained via active immunization of animals. For this purpose, for example, suitable animals (e.g. rabbits) receive a series of injections of the appropriate antigen. The animals' immune system generates corresponding antibodies, which are collected from the animals in a known manner. This procedure enables preparation of a monospecific antibody-rich serum.

If desired, the serum containing antibodies may be purified, for example by using affine chromatography, fractionation by salt precipitation, or ion-exchange chromatography.

The resulting purified, antibody-enriched serum may be used as a starting material for the preparation of the activated-potentiated form of the antibodies. The preferred concentration of the resulting initial solution of antibody in the solvent, preferably water or a water-ethyl alcohol mixture, ranges from about 0.5 to about 5.0 mg/ml.

The preferred procedure for preparing each component of the combination drug according to the present invention is the use of the mixture of three aqueous-alcohol dilutions of the primary matrix solution of antibodies diluted $100^{12}$, $100^{30}$ and $100^{50}$ times, respectively, which is equivalent to centesimal homeopathic dilutions C12, C30, and C50 or diluted $100^{12}$, $100^{30}$ and $100^{200}$ times, respectively, which is equivalent to centesimal homeopathic dilutions C12, C30 and C200. To prepare a solid dosage form, a solid carrier is treated with the desired dilution obtained via the homeopathic process. To obtain a solid unit dosage form of the combination of the invention, the carrier mass is impregnated with each of the dilutions. Any order of impregnation of the solid carrier to prepare the desired combination solid dosage form is specifically contemplated, including sequential impregnation of the carrier in any sequence with the requisite final dilution or mixture of dilutions, as well as impregnation of the carrier with the liquid mixture of all components.

In a preferred embodiment, the starting material for the preparation of the activated-potentiated form that comprises the combination of the invention is polyclonal, animal-raised antibody to the corresponding antigen.

The exemplary procedure for preparation of the starting polyclonal antibodies may be described as follows. In 7-9 days before blood sampling, 1-3 intravenous injections of the desired antigen are made to the rabbits to increase the level of polyclonal antibodies in the rabbit blood stream. Upon immunization, blood samples are taken to test the antibody level. Typically, the maximum level of immune reaction of the soluble antigen is achieved within 40 to 60 days after the first injection of the antigen. Upon completion of the first immunization cycle, rabbits have a 30-day rehabilitation period, after which re-immunization is performed with another 1-3 intravenous injections.

To obtain antiserum containing the desired antibodies, the immunized rabbits' blood is collected from rabbits and placed in a 50 ml centrifuge tube. Product clots formed on the tube sides are removed with a wooden spatula, and a rod is placed into the clot in the tube center. The blood is then placed in a refrigerator for one night at the temperature of about 40° C. On the following day, the clot on the spatula is removed, and the remaining liquid is centrifuged for 10 min at 13,000 rotations per minute. Supernatant fluid is the target antiserum. The obtained antiserum is typically yellow. 20% of $NaN_3$ (weight concentration) is added in the antiserum to a final concentration of 0.02% and stored before use in frozen state at the temperature of −20° C., or without $NaN_3$ at the temperature of −70° C. To separate the target antibodies from the antiserum, the following solid phase absorption sequence is suitable:

10 ml of the antiserum of rabbits is diluted twofold with 0.15 M NaCl, after which 6.26 g $Na_2SO_4$ is added, mixed and incubated for 12-16 hours at 4° C. The sediment is removed by centrifugation, diluted in 10 ml of phosphate buffer and dialyzed against the same buffer during one night at ambient temperature. After the sediment is removed, the solution is applied to a DEAE-cellulose column balanced by phosphate buffer. The antibody fraction is determined by measuring the optical density of the eluate at 280 nm.

The isolated crude antibodies may be purified using affine chromatography method by attaching the obtained antibodies to the insoluble matrix of the chromatography media, with subsequent elution by concentrated aqueous salt solutions.

The resulting buffer solution is used as the initial solution for the homeopathic dilution process used to prepare the activated potentiated form of the antibodies.

The activated potentiated form of each component of the combination may be prepared from an initial solution by homeopathic potentization, preferably using the method of proportional concentration decrease by serial dilution of 1 part of each preceding solution (beginning with the initial solution) in 9 parts (for decimal dilution), or in 99 parts (for centesimal dilution), or in 999 parts (for millesimal dilution) of a neutral solvent, starting with a concentration of the initial solution of antibody in the solvent, preferably, water or a water-ethyl alcohol mixture, in the range from about 0.5 to about 5.0 mg/ml, coupled with external impact. Preferably, the external impact involves multiple vertical shaking (dynamization) of each dilution. Preferably, separate containers are used for each subsequent dilution up to the required potency level, or the dilution factor. This method is well-accepted in the homeopathic art. See, e.g. V. Schwabe "*Homeopathic medicines*", M., 1967, p. 14-29, incorporated herein by reference for the purpose stated.

For example, to prepare a 12-centesimal dilution (denoted C12), one part of the initial matrix solution of antibodies to histamine with the concentration of 3.0 mg/ml is diluted in 99 parts of neutral aqueous or aqueous-alcohol solvent (preferably, 15%-ethyl alcohol) and then vertically shaked many times (10 and more) to create the 1st centesimal dilution (denoted as C1). The 2nd centesimal dilution (C2) is prepared from the 1st centesimal dilution C1. This procedure is repeated 11 times to prepare the 12th centesimal dilution C12. Thus, the 12th centesimal dilution C12 represents a solution obtained by 12 serial dilutions of one part of the initial matrix solution of antibodies with the concentration of 3.0 mg/ml in 99 parts of a neutral solvent in different containers, which is equivalent to the centesimal homeopathic dilution C12. Similar procedures with the relevant dilution factor are performed to obtain the desired dilutions. The intermediate dilutions may be tested in a desired biological model to check activity. The preferred activated potentiated forms for antibodies comprising the combination of the invention is a C12, C30 and C200 dilutions for each activated-potentiated form. When using the mixture of various homeopathic dilutions (primarily centesimal) of the active substance as biologically active liquid component, each component of the composition (e.g., C12, C30, C50, C200) is prepared separately according to the above-described procedure until the next-to-last dilution is obtained (e.g., until C11, C29, and C199 respectively), and then one part of each component is added in one container according to the mixture composition and mixed with the required quantity of the solvent (e.g. with 97 parts for centesimal dilution).

It is possible to use the active substance as mixture of various homeopathic dilutions, e.g. decimal and/or centesimal (D20, C30, C100 or C12, C30, C50 or C12, C30, C200, etc.), the efficiency of which is determined experimentally by testing the dilution in a suitable biological model, for example, in models described in the examples herein.

In the course of potentiation and concentration decrease, the vertical shaking may be substituted for external exposure to ultrasound, electromagnetic field or any similar external impact procedure accepted in the homeopathic art.

The solid unit dosage form of the pharmaceutical composition of the invention may be prepared by using impregnating a solid, pharmaceutically acceptable carrier with the mixture of the activated potentiated form aqueous or aqueous-alcohol solutions of active components that are mixed, primarily in 1:1:1 ratio and used in liquid dosage form. Alternatively, the carrier may be impregnated consecutively with each requisite dilution.

Preferably, the pharmaceutical composition in the solid unit dosage form is prepared from granules of the pharmaceutically acceptable carrier which was previously saturated with the aqueous or aqueous-alcoholic dilutions of the activated potentiated form of antibodies. The solid dosage form may be in any form known in the pharmaceutical art, including a tablet, a capsule, a lozenge, and others. As an inactive pharmaceutical ingredients one can use glucose, sucrose, maltose, amylum, isomaltose, isomalt and other mono-oligo- and polysaccharides used in manufacturing of pharmaceuticals as well as technological mixtures of the above mentioned inactive pharmaceutical ingredients with other pharmaceutically acceptable excipients, for example isomalt, crospovidone, sodium cyclamate, sodium saccharine, anhydrous citric acid etc), including lubricants, disintegrants, binders and coloring agents. The preferred carriers are lactose and isomalt. The pharmaceutical dosage form may further include standard pharmaceutical excipients, for example, microcrystalline cellulose and magnesium stearate.

The example of preparation of the solid unit dosage form is set forth below. To prepare the solid oral form, 100-300 μm granules of lactose are impregnated with aqueous or aqueous-alcoholic solutions of the activated potentiated form of antibodies to histamine, activated-potentiated form of antibodies to TNF-α and the activated potentiated form of antibodies to protein S-100 in the ratio of 1 kg of antibody solution to 5 or 10 kg of lactose (1:5 to 1:10). To effect impregnation, the lactose granules are exposed to saturation irrigation in the fluidized boiling bed in a boiling bed plant (e.g. "Hüttlin Pilotlab" by Hüttlin GmbH) with subsequent drying via heated air flow at a temperature below 40° C. The estimated quantity of the dried granules (10 to 34 weight parts) saturated with the activated potentiated form of antibodies is placed in the mixer, and mixed with 25 to 45 weight parts of "non-saturated" pure lactose (used for the purposes of cost reduction and simplification and acceleration of the technological process without decreasing the treatment efficiency), together with 0.1 to 1 weight parts of magnesium stearate, and 3 to 10 weight parts of microcrystalline cellulose. The obtained tablet mass is uniformly mixed, and tableted by direct dry pressing (e.g., in a Korsch—XL 400 tablet press) to form 150 to 500 mg round pills, preferably, 300 mg. After tableting, 300 mg pills are obtained that are saturated with aqueous-alcohol solution (3.0-6.0 mg/pill) of the combination of the activated-potentiated form of antibodies. Each component of the combination used to impregnate the carrier is in the form of a mixture of centesimal homeopathic dilutions, preferably, C12, C30 and C200.

While the invention is not limited to any specific theory, it is believed that the activated-potentiated form of the antibodies described herein do not contain the molecular form of the antibody in an amount sufficient to have biological activity attributed to such molecular form. The biological activity of the combination drug (combination pharmaceutical composition) of the invention is amply demonstrated in the appended examples.

Preferably, for the purpose of treatment, the combination of the invention is administered from once daily to four times daily, preferably twice daily, each administration including one or two combination unit dosage forms.

The invention is further illustrated with reference to the appended non-limiting examples.

EXAMPLES

Example 1

Three experimental studies investigated the effects of i) ultra-low doses of antibodies to histamine (His Ab), affinely purified on antigen, obtained by hyper-dilution of the initial matrix solution (mixture of $100^{12}$, $100^{30}$, $100^{200}$ dilutions (C12, C30 and C200), and ii) a combination of a) ultra-low doses of antibodies to histamine (His Ab), affinely purified on antigen, obtained by hyper-dilution of the initial matrix solution (mixture of $100^{12}$, $100^{30}$, $100^{200}$ dilutions (C12, C30 and C200) with b) ultra-low doses of antibodies to protein S-100 (S-100 Ab), affinely purified on antigen, obtained by hyper-dilution of the initial matrix solution (mixture of $100^{12}$, $100^{30}$, $100^{200}$ dilutions (C12, C30 and C200)) and c) ultra-low doses of antibodies to tumor necrosis factor alpha (TNF Ab), affinely purified on antigen, obtained by hyperdilution of the initial matrix solution (mixtire of $100^{12}$, $100^{30}$, $100^{200}$ dilutions (C12, C30, and C200)) (S100 Ab+TNF Ab+His Ab).

Study 1. Effect on Motor-Evacuation Function of Gastrointestinal Tract (GIT) of Mice 31 outbred male mice (mass 17.5-26.3 g, age 1.5-2 months) were intragastrically injected with either distilled water (control, 15 ml/kg), or His Ab (15 ml/kg), or S100 Ab+TNF Ab+His Ab (15 ml/kg) over 5 days. The state of the motor-evacuation function of the stomach and intestine was studied by the "markers" method [Coopman, G. P., Kennis, H. M., Two Methods to Assess the gastrointestinal transit-time in micell Z. Vershuchstierk, Vol. 19, No. 5, pp. 298-303, 1977, incorporated herein by reference]. 1 hour after the last injection, a 10% suspension of activated charcoal, prepared on 2% potato starch slime, in the amount of 0.5 ml/mouse had been injected in the digestive tract of the mice as a "marker." Within 10 minutes of the injection of the "marker," the stomach and the intestines were recovered and spread out on a glass plate. The overall length of the intestine filled with the marker was measured (namely, the ratio of the length of activated charcoal filled part of intestine to overall length, expressed as percentages).

It was established that injection of the S100 Ab+TNF Ab+His Ab combination at the dose of 15 ml/kg led to a statistically significant increase in the overall path length of the activated charcoal along the intestine 1.3 and 1.2 times relative to the corresponding values of the His Ab and distilled water (control) groups, respectively (Table 1). For combination S100 Ab+TNF Ab+His Ab, the ratio of the length of the coal-filled portion to the overall length of the intestine also exceeded the analogous indicators in the His Ab group ($p<0.05$) and control group ($p<0.05$).

Thus, it was shown that the combination S100 Ab+TNF Ab+His Ab strengthens the motor-evacuation activity of the GIT of mice with the effect exceeding the efficacy of His Ab.

TABLE 1

Effect of tested preparations on motor-evacuation activity of GIT of outbred male mice

| Experimental group (number of animals) | Length of coal filled portion of intestine per mouse (M ± m), cm | Ratio of the length of coal filled portion to the overall length of intestine (M ± m), % |
|---|---|---|
| Dist. water (n = 10) | 25.4 ± 1.49 | 44.1 ± 2.77 |
| His Ab (n = 11) | 24.1 ± 1.92 | 44.9 ± 3.65 |
| S100 Ab + TNF Ab + His Ab (n = 10) | 31.1 ± 2.09*# | 54.4 ± 3.24*# |

*differences are statistically significant in reference to control ($p < 0.05$)
differences are statistically significant in reference to His Ab group ($p < 0.05$).

Study 2. Effect on Secretory Function of GIT of Mice 33 outbred male mice (mass 17.5-26.3 g, age 1.5-2 months) were intragastrically injected four times with either distilled water (control, 15 ml/kg), or His Ab (15 ml/kg) or S100 Ab+TNF Ab+His Ab (15 ml/kg). The state of the intestine secretory function was studied with the G. V. Obolentsev method (G. V. Oboletsev, Y. I. Hadzhai, Pharmacological investigation of plantagluside, Pharmacology and toxicology (in Russian), No. 4, pp. 469-472, 1996, incorporated herein by reference). Each test preparation was injected together with activated charcoal in the dose of 10 mg/kg. The appearance of feces painted with coal of black color was considered a positive. Measurements were carried out 3, 6, and 24 hours from the start of the experiment. The magnitude and/or nature of the effect for each animal was denoted as follows: "+" —appearance of well-formed darkened feces; "++" —appearance of soft darkened feces; "+++" —appearance of liquid darkened feces. The laxative activity was evaluated by total points in the group according to the percentage of animals with a positive reaction.

TABLE 2

Effect of tested preparations on intestine excretory function in outbred male mice

| Observation group, (number of animals) | Magnitude of effect (points/% of animals with reaction) | | |
|---|---|---|---|
| | 3 hr | 6 hr | 24 hr |
| | Four-times injection of the preparations | | |
| Control (n = 11) | 22/100 | 18/100 | 7/55 |
| His Ab (n = 11) | 18/100 | 18/100 | 6/55 |
| S100 Ab + TNF Ab + His Ab (n = 11) | 25/100 | 24/100 | 6/55 |

A certain strengthening of peristalsis was observed in the first 3 hours after the injection of S100 Ab+TNF Ab+His Ab as follows: 25 points for the combination versus 18 points in the His Ab group and 22 points in the control group (Table 2). The effect was retained for the S100 Ab+TNF Ab+His Ab group over 6 hours of observation: 24 points for combination versus 18 points for the His Ab and control groups. Within 24 hours, there was a noted reduction in the excretory activity in all three experimental groups, including absence of defecation in 45% of animals.

Thus, it was shown that the combination S100 Ab+TNF Ab+His Ab possesses a laxative effect which exceeds the effect of His Ab.

Study 3. Spasmolytic Activity 30 outbred male mice (mass 17.5-26.3 g, age 1.5-2 mo), were intragastrically injected over 5 days with either distilled water (control, 15 ml/kg), or His Ab (15 ml/kg) or S100 Ab+TNF Ab+His Ab (15 ml/kg). The spasmolytic activity of the preparations was evaluated according to the J. Setnicar method (1959)[Senticar J., Da Re P., 3-methyl-6-(N-diethyl-amino-methyl)-Flavone-a new smooth muscle relaxant//Arzneimittel-Forsch, No. 9, pp. 653-697 (1959)), incorporated herein by reference]. 1 hour after the last injection, the mice were intraperitoneally injected with 0.2 ml of 0.1% $BaCl_2$ solution and intragastrically with 0.5 ml of a 10% suspension of activated charcoal prepared on 2% potato starch slime. After 10 minutes, the animals were sacrificed. The ratio between the overall length of the intestine and the portion filled with coal was then determined. The ratio was expressed in percentages and considered as the primary experimental result.

In the group which received the S100 Ab+TNF Ab+His Ab combination, the maximum distance that the coal advanced along the intestine was 1.3 times greater relative to the His Ab and control group (Table 3). GIT spasm caused by the injection of $BaCl_2$ leading to the reduction in the speed of advance of activated charcoal along the intestine was least expressed in the S100 Ab+TNF Ab+His Ab group.

TABLE 3

Evaluation of spasmolytic effect of test preparations by "carbon markers" method (with $BaCl_2$)

| Observation group, (number of animals) | Length of coal filled portion of the intestine per mouse (M ± m), cm | Ratio of the length of coal filled portion to overall length of intestine (M ± m), % |
|---|---|---|
| Control, (n = 10) | 23.3 ± 2.20 | 42.4 ± 3.49 |
| His Ab, (n = 10) | 22.3 ± 2.09 | 40.1 ± 3.81 |
| S100 Ab + TNF Ab + His Ab, (n = 10) | 30.0 ± 2.42*# | 56.4 ± 4.50*# |

*differences are statistically significant in reference to control (p < 0.05)
differences are statistically significant in reference to His Ab group (p < 0.05)

Thus, it was shown that the combination S100 Ab+TNF Ab+His Ab possesses spasmolytic effect which exceeds the efficacy of His Ab.

Example 2

300 mg tablets were prepared by impregnation of the lactose carrier by water-alcohol solutions (6 mg/tab) of ultra-low doses of affinely purified polyclonal rabbit antibodies to human tumor necrosis factor alpha (TNF Ab), brain-specific protein S-100 (S100 Ab) and histamine (His Ab). Each of the components used for the impregnation was obtained by hyper-dilution of the initial matrix solution with concentration of 2.5 mg/ml $100^{12}$, $100^{30}$, $100^{200}$ times (mixtures of centesimal homeopathic dilutions C12, C30, C200). For the comparison group, 300 mg other tablets were used, saturated with a water-alcohol solution (3 mg/tab) of the ultra-low doses of polyclonal rabbit antibodies to histamine, purified on antigen, (F is Ab), obtained by hyper-dilution of the initial matrix solution with concentration of 2.5 mg/ml $100^{12}$, $100^{30}$, $100^{200}$ times (mixture of centesimal homeopathic dilutions C12, C30, C200).

52 patients participating in the study had verified diagnosis of irritable bowel syndrome (IBS) in accordance with Roman Criteria III (2006). The patients enrolled in the study participated in an outpatient course of observation and therapy over 12 weeks. 24 study participants were included in the test preparation group (TNF Ab+S100 Ab+His Ab, 2 tablets 2 times a day). 28 patients were included in the comparison group (His Ab, 2 tablets 2 times a day). Both groups of patients were comparable in the relevant initial demographic, anthropometric and clinical laboratory indicators. 18 patients had IBS with constipation (solid or lumpy stool comprised more than 25% and liquid stool less than 25% of all bowel evacuations), 14 patients had IBS with diarrhea (paste-like or liquid stool comprising more than 25% and solid stool of less than 25% of all bowel evacuations), and 20 patients had mixed version of IBS (both lumpy stool and liquid stool comprised more than 25% of all bowel evacuations). Therapy efficacy criteria took into account the following parameters: the reduction in the intensity of pain/discomfort (average value for week, from 0 to 10 points) in comparison with the initial state, the dynamics of other dyspeptic symptoms on the VAS-IBS scale (Visual Analogue Scale—Irritable Bowel Syndrome (VAS-IBS): Guidance for Industry Irritable Bowel Syndrome—Clinical Evaluation of Products for Treatment. U.S. Department of Health and Human Services, Food and Drug Administration; Center for Drug Evaluation and Research (CDER)—March 2010; Muller-Lissner, S., Koch, G., Talley, N.J., et al., 2004, Subject's Global Assessment of Relief: An Appropriate Method to Assess the Impact of Treatment on IBS-Related Symptoms in Clinical Trials, J Clin. Epidemiol, 56:310-316; CPMP/EWP/785/97, 2003, Points to Consider on the Evaluation of Medicinal Products for 483 the Treatment of Irritable Bowel Syndrome, London); change in the visceral sensitivity index (worst—15, best—90) on the VSI scale (Visceral Sensitivity Index (VSI): Labus, S. Jennifer, et al. The Central Role of Gastrointestinal-Specific Anxiety in Irritable Bowel Syndrome: Further Validation of the Visceral Sensitivity Index. Psychomotor Medicine, 2007; 69:89-98.), and evaluation on the HADS scale (Hospital Anxiety and Depression Scale (HADS): Snaith, R. Philip. The Hospital Anxiety and Depression Scale. Health and Quality of Life Outcomes 2003, 1:1-4). In patients with IBS with predominance of diarrhea, the portion of patients with a change in stool type was calculated on the Bristol scale of stool form (Bristol scale of stool form: Guidance for Industry Irritable Bowel Syndrome—Clinical Evaluation of Products for Treatment. U.S. Department of Health and Human Services, Food and Drug Administration; Center for Drug Evaluation and Research (CDER)—March 2010.) up to 5 (but not lower than ≤2 on average for the week); in patients in the IBS subgroup with predominance of constipation, the percentage of patients with an increase in the number of acts of defecation on average by 1 time a week in comparison with the initial state of the patients.

In the clinical picture of the disease in both groups, abdominal pain syndrome was predominant (average of 7.56±0.26 points in for the combination group and 7.21±0.24 for the comparison group by VAS-IBS) (see table). This symptom was encountered in 100% of patients at the initial examination. Among dyspetic manifestations, equally frequently were diarrhea (in 54% of patients in the active preparation group and 57% of patients in the comparison group) and constipation (62% and 57%, respectively), bulging stomach and flatulence (in 46% and 36%, respectively), whose manifestation was approximately identical in both groups (see table). Nausea and vomiting were encountered more rarely (30% and 32%, respectively). The average values of the visceral sensitivity index (VSI) and HADS scale indicator were similar for both groups (see table), pointing to the significant effect of central nervous system disturbance in the development of IBS. The patients of both groups were permitted to take the laxative Guttalax® and antidiarrheal drug Smecta® for constipation or diarrhea, respectively. The preparation No-shpa® for reducing the manifestation of spastic pains in the stomach was also permitted. These preparations were taken by patients as needed. All patients of the groups being investigated completed treatment in the time periods established by the study protocol, no patients dropped out early.

TABLE 4

Dynamics of basic indicators depending on form of therapy

| Period | TNF-α Ab + S100 Ab + His Ab (n = 24; M ± SE) | His Ab (n = 28; M ± SE) |
|---|---|---|
| VAS-IBS: pain/discomfort, points | | |
| Initial | 7.56 ± 0.26 | 7.21 ± 0.24 |
| 12 weeks | 3.32 ± 0.13* ** | 5.64 ± 0.24** |
| VAS-IBS: diarrhea, points | | |
| Initial | 5.52 ± 0.18 | 5.73 ± 0.34 |
| 12 weeks | 3.34 ± 0.22* | 4.86 ± 0.22 |
| VAS-IBS: constipation, points | | |
| Initial | 5.79 ± 0.26 | 4.98 ± 0.34 |
| 12 weeks | 4.41 ± 0.33** | 4.25 ± 0.26 |
| VAS-IBS: bulging stomach and flatulence, points | | |
| Initial | 4.98 ± 0.34 | 4.57 ± 0.31 |
| 12 weeks | 3.84 ± 0.24** | 4.04 ± 0.31 |
| VAS-IBS: vomiting and nausea, points | | |
| Initial | 3.94 ± 0.31 | 3.56 ± 0.24 |
| 12 weeks | 2.87 ± 0.12* | 3.03 ± 0.27 |
| Visceral Sensitivity Index (VSI-IBS), points | | |
| Initial | 22.3 ± 1.6 | 25.4 ± 1.8 |
| 12 weeks | 68.7 ± 2.4* ** | 33.9 ± 1.7 |
| Hospital Anxiety and Depression Scale (HADS), points | | |
| Initial | 19.3 ± 1.4 | 18.9 ± 1.5 |
| 12 weeks | 12.8 ± 0.6* ** | 14.4 ± 1.3 |

*Difference between TNF-α Ab + S100 Ab + His Ab and His Ab groups are statistically significant with $p < 0.05$.
**Difference with the initial indicator is statistically significant with $p < 0.05$.

The analysis of the data showed that during the 12-week therapy the expression of the basic clinical manifestation of IBS, abdominal pain syndrome, was reduced in patients of the group taking the combination His Ab+S100 Ab+TNF Ab by more than 50% in comparison with the initial condition of the patients (3.32±0.13 points). This reduction was significantly different in comparison with the treatment outcomes obtained through the use of His Ab alone, which also promoted a decrease in the manifestation of pain/discomfort but to a significantly lesser degree (less than 30%).

The test combination favorably affected other dyspeptic disorders in patients, including diarrhea (reduction from the initial values of 5.52±0.18 points to 3.34±0.22 points at the end of the therapy), constipation (5.79±0.26 and 4.41±0.33 points, respectively), bulging stomach and flatulence (4.98±0.34 and 3.84±0.24 points, respectively). In addition, the efficacy with respect to the latter two symptoms was statistically significant in comparison with both the initial condition of the patients and with the efficacy of His Ab alone.

In the subgroup of patients with IBS with predominance of diarrhea (n=14), the portion of patients which exhibited a change in stool type on the Bristol scale of stool form up to 5 or less points was 57% for the combination group; in the IBS subgroup with predominance of constipation (n=18), the percentage of patients with an increase in the number of acts of defecation on average by 1 time a week reached 94%; among patients with a mixed version of IBS (n=20), analogous indicators were 45% and 75%, respectively. Among patients of the comparison group, the indicators studied could not be considered significant.

The efficacy of treatment with the combination preparation was manifested in the positive effect on visceral hypersensitivity, which was significantly reduced over the 12 weeks with the VSI index increasing from 22.3±1.6 to 68.7±2.4 (versus 25.4±1.8 and 33.9±1.7, respectively, in the comparison group). Positive changes observed with the combination preparation were also manifested in the decrease in total points on the HADS scale (from 19.3±1.4 to 12.8±0.6), which attested to curtailing of initial subclinically expressed anxiety and depression.

Evaluation of the safety of the therapy, conducted on the basis of the record of adverse events in the period of treatment and follow-up study of laboratory indicators, testified to the good tolerance of the preparations. The safety analysis included data of all patients who participated in the study (n=52). During the 12-week course of treatment, no patient of either groups manifested any adverse events which had "possible" or "obvious" connection with taking of the medicine. Laboratory studies, including general and biochemical blood analyses and clinical urine analysis, also did not record any pathologic deviations in the course of therapy.

Thus, the study demonstrated the efficacy and safety of the combination of ultra-low doses of TNF Ab+S100 Ab+His Ab in the treatment of patients with IBS. It was shown that 12-week of taking the combination promoted curtailing of abdominal pain syndrome and also significant decrease in the expression of dyspeptic manifestations in patients with IBS. The effect of treatment was confirmed by the high percentage of patients who improved bowel evacuation indicators. Besides positive dynamics of basic symptoms on the part of the gastrointestinal tract, there was noted natural normalization of the somatic and mental condition of the patient, which was expressed in positive changes in visceral sensitivity and leveling of symptoms of anxiety and depression. The effects of the therapy with the combination of ultra-low doses of TNF Ab+S100 Ab+His Ab had significant differences in comparison with the initial condition of the patients and His Ab alone.

What is claimed is:

1. A combination pharmaceutical composition comprising a) an activated-potentiated form of an antibody to S-100 protein, b) an activated-potentiated form of an antibody to histamine, and c) an activated-potentiated form of an antibody to TNF-alpha.

2. The combination pharmaceutical composition of claim 1, which further comprises a solid carrier, wherein said activated-potentiated form an antibody to S-100 protein, said activated-potentiated form of an antibody to histamine, and said activated-potentiated form of an antibody to TNF-alpha are impregnated onto said solid carrier.

3. The combination pharmaceutical composition of claim 2, which is in the form of a tablet.

4. The combination pharmaceutical composition of claims 1, wherein said activated-potentiated form of an antibody to S-100 protein is in the form of a mixture of C12, C30, and C200 homeopathic dilutions.

5. The combination pharmaceutical composition of claim 1, wherein said activated-potentiated form of an antibody to histamine is in the form of a mixture of C12, C30, and C200 homeopathic dilutions.

6. The combination pharmaceutical composition of claim 1, wherein said activated-potentiated form of an antibody to TNF-alpha is in the form of a mixture of C12, C30, and C200 homeopathic dilutions.

7. The combination pharmaceutical composition of claim 1, wherein the activated-potentiated form of an antibody to histamine is a monoclonal or polyclonal antibody.

8. The combination pharmaceutical composition of claim 7, wherein the activated-potentiated form of an antibody to histamine is a polyclonal antibody.

9. The combination pharmaceutical composition of claim 1, wherein the activated-potentiated form of an antibody to S-100 protein is a monoclonal or polyclonal antibody.

10. The combination pharmaceutical composition of claim 9, wherein the activated-potentiated form of an antibody to S-100 protein is a polyclonal antibody.

11. The combination pharmaceutical composition of claim 1, wherein the activated-potentiated form of an antibody to TNF-alpha is a monoclonal or polyclonal antibody.

12. The combination pharmaceutical composition of claim 11, wherein the activated-potentiated form of an antibody to TNF-alpha is a polyclonal antibody.

13. The combination pharmaceutical composition of claim 1, wherein the activated-potentiated form of an antibody to a TNF-alpha is to the entire molecule of TNF-alpha having SEQ ID NO. 1.

14. The combination pharmaceutical composition of claim 1, wherein the activated-potentiated form of an antibody to a TNF-alpha is to a fragment of TNF-alpha having a sequence selected from group consisting of SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, and SEQ ID NO. 12.

15. The combination pharmaceutical composition of claim 1, wherein the activated-potentiated form of an antibody to protein S-100 is an antibody to bovine S-100 protein.

16. The combination pharmaceutical composition of claim 1, wherein the activated-potentiated form of an antibody to protein S-100 is to the entire S-100 protein having SEQ ID NO 13.

17. The combination pharmaceutical composition of claim 1, wherein the activated-potentiated form of an antibody to protein S-100 is to the entire S-100 protein having SEQ ID NO 16.

18. The combination pharmaceutical composition of claim 1, wherein said activated-potentiated forms of an antibody are prepared by successive centesimal dilutions coupled with shaking of every dilution.

19. The combination pharmaceutical composition of claim 1, wherein said activated-potentiated form of an antibody to S-100, said activated-potentiated form of an antibody to histamine, and said activated-potentiated form of antibody to TNF-alpha are impregnated onto a solid carrier.

* * * * *